United States Patent [19]
Buzzetti et al.

[11] Patent Number: 5,719,135
[45] Date of Patent: Feb. 17, 1998

[54] SUBSTITUTED 3-ARYLIDENE-7-AZAOXINDOLE COMPOUNDS AND PROCESS FOR THEIR PREPARATION

[75] Inventors: Franco Buzzetti, Monza; Gabriella Maria Brasca, Cusago; Antonio Longo, Milan; Dario Ballinari, San Donato Milanese, all of Italy

[73] Assignee: Pharmacia S.p.A., Milan, Italy

[21] Appl. No.: 669,315

[22] PCT Filed: Oct. 30, 1995

[86] PCT No.: PCT/EP95/04247

§ 371 Date: Jul. 9, 1996

§ 102(e) Date: Jul. 9, 1996

[87] PCT Pub. No.: WO96/16964

PCT Pub. Date: Jun. 6, 1996

[30] Foreign Application Priority Data

Nov. 28, 1994 [GB] United Kingdom ............... 9423997

[51] Int. Cl.$^6$ .................. A61K 31/675; A61K 31/44; C07D 401/00; C07D 471/02
[52] U.S. Cl. .................. 514/81; 514/234.5; 514/255; 514/300; 544/127; 544/362; 546/21; 546/23; 546/113
[58] Field of Search ............... 546/21, 23, 113; 544/127, 362; 514/81, 234.5, 255, 300

[56] References Cited

FOREIGN PATENT DOCUMENTS

WO 94/14808  7/1994  WIPO .

*Primary Examiner*—Mukund J. Shah
*Assistant Examiner*—Brenda Coleman
*Attorney, Agent, or Firm*—Oblon, Spivak, McClelland, Maier & Neustadt, P.C.

[57] ABSTRACT

The present invention relates to compound of formula (I)

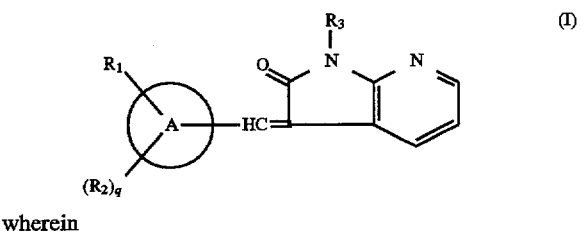

wherein

A is benzene, naphthalene, 5,6,7,8,-tetrahydronaphthalene, quinoline, isoquinoline, indole or 7-azaindole;

$R_1$ is —H, —CN, —$SO_3R_4$—, —$SO_2NHR_5$,

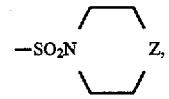

—$COOR_6$, —$CONHCH_2(CHOH)_nCH_2OH$,

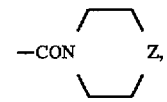

—$NR_7R_8$, —$N(CH_2CH_2OH)_2$, —$NHCH_2(CHOH)_nCH_2OH$, —$NHCONH_2$, —NH—$C(NH_2)$=NH, —$NHCO(CHOH)_nCH_2OH$,

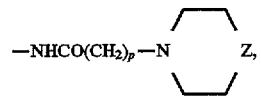

—$NHSO_2R_9$, —$OR_{10}$, —$OCH_2(CHOH)_nCH_2OH$, —$OOC(CHOH)_nCH_2OH$, —$OPO(OH)_2$, —$CH_2NH_2$, —$C(NH_2)$=NH, —$CH_2NHC(NH_2)$=NH,

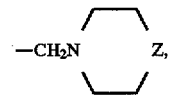

—$CH_2OH$, —$CH_2OOC(CHOH)_nCH_2OH$, —$CH_2OPO(OH)_2$ or —$PO(OH)_2$;

$R_2$ is $C_1$–$C_6$ alkyl, halogen, or hydroxy;
$R_3$ is —H or $C_1$–$C_6$ alkyl;
$R_4$ is —H, $C_1$–$C_6$ alkyl or —$CH_2(CHOH)_nCH_2OH$;
$R_5$ is —H, $C_1$–$C_6$ alkyl, —$CH_2(CHOH)_nCH_2OH$ or —$(CH_2)_mNMe_2$;
$R_6$ is —H, $C_1$–$C_6$ alkyl or —$CH_2(CHOH)_nCH_2OH$;
each of $R_7$ and $R_8$ independently is —H or $C_1$–$C_6$ alkyl;
$R_9$ is methyl or tolyl;
$R_{10}$ is —H, $C_1$–$C_6$ alkyl, or $C_2$–$C_6$ alkanoyl;
Z is >$CH_2$, >O, >NH, or >$NCH_2CH_2OH$; n is zero or 1; m is 2 or 3; p is 1, 2 or 3; q is zero, 1 or 2;
and the pharmaceutically acceptable salt thereof, for use as tyrosine kinase inhibitors.

12 Claims, No Drawings

SUBSTITUTED 3-ARYLIDENE-7-AZAOXINDOLE COMPOUNDS AND PROCESS FOR THEIR PREPARATION

This application is a 371 of PCT/EP95/04247, filed Oct. 30, 1995.

The present invention relates to 3-arylidene-7-azaoxindole compounds, to a process for their preparation, to pharmaceutical compositions containing them and to their use as therapeutic agents.

The present invention provides compounds having the following general formula (I)

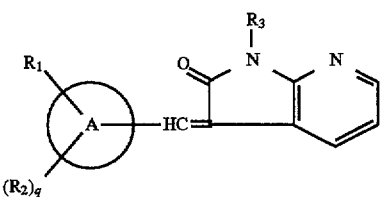

wherein

A is benzene, naphthalene, 5,6,7,8,-tetrahydronaphthalene, quinoline, isoquinoline, indole or 7-azaindole;

$R_1$ is —H, —CN, —$SO_3R_4$, —$SO_2NHR_5$,

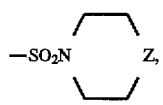

—COO$R_6$, —CONHCH$_2$(CHOH)$_n$CH$_2$OH,

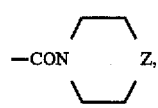

—NR$_7$R$_8$, —N(CH$_2$CH$_2$OH)$_2$, —NHCH$_2$(CHOH)$_n$CH$_2$OH, —NHCONH$_2$, —NH—C(NH$_2$)=NH, —NHCO(CHOH)$_n$CH$_2$OH,

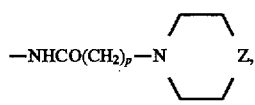

—NHSO$_2$R$_9$, —OR$_{10}$, —OCH$_2$(CHOH)$_n$CH$_2$OH, —OOC(CHOH)$_n$CH$_2$OH, —PO(OH)$_2$, —CH$_2$NH$_2$, —C(NH$_2$)=NH, —CH$_2$NHC(NH$_2$)=NH,

—CH$_2$OH, —CH$_2$OOC(CHOH)$_n$CH$_2$OH, —CH$_2$OPO(OH)$_2$ or —PO(OH)$_2$;

$R_2$ is $C_1$-$C_6$ alkyl, halogen, or hydroxy;
$R_3$ is —H or $C_1$-$C_6$ alkyl;
$R_4$ is —H, $C_1$-$C_6$ alkyl or —CH$_2$(CHOH)$_n$CH$_2$OH;
$R_5$ is —H, $C_1$-$C_6$ alkyl, —CH$_2$(CHOH)$_n$CH$_2$OH or —(CH$_2$)$_m$NMe$_2$;
$R_6$ is —H, $C_1$-$C_6$ alkyl or —CH$_2$(CHOH)$_n$CH$_2$OH;
each of $R_7$ and $R_8$ independently is —H or $C_1$-$C_6$ alkyl;
$R_9$ is methyl or tolyl;
$R_{10}$ is —H, $C_1$-$C_6$ alkyl or $C_2$-$C_6$ alkanoyl;
Z is >CH$_2$, >O, >NH or >NCH$_2$CH$_2$OH;
n is zero or 1;
m is 2 or 3;
p is 1, 2 or 3;
q is zero, 1 or 2;
and the pharmaceutically acceptable salt thereof.

The invention includes within its scope all the possible isomers, stereoisomers, in particular Z- and E-isomers, as well as the metabolites and the metabolic precursors or bio-precursors (otherwise known as pro-drugs) of the compounds of formula (I).

The substituents $R_1$ and $R_2$ may be independently on either of the ring moieties when A is bicyclic.

The azaoxindolylidene substituent is preferably linked to position 1 or 2 when A is naphthalene or 5,6,7,8-tetrahydronaphthalene, to position 4 or 5 when A is quinoline, to position 1 or 3 when A is isoquinoline, to position 3 when A is indole, or 7-azaindole.

The $R_1$ substituent with reference to the azaoxindolylidene substituent is preferably linked to the other ring moiety when A is naphthalene, 5,6,7,8-tetrahydronaphthalene, quinoline, isoquinoline, indole or azaindole.

The alkyl group and the alkyl moiety in the alkanoyl group may be branched or straight alkyl chains.

A $C_1$-$C_6$ alkyl group is preferably a $C_1$-$C_4$ alkyl group, e.g. methyl, ethyl, propyl, isopropyl, butyl, sec-butyl or t-butyl, in particular methyl or ethyl.

A $C_2$-$C_6$ alkanoyl group is preferably a $C_2$-$C_3$ alkanoyl group, in particular acetyl or propionyl.

A halogen is preferably fluorine, chlorine or bromine, in particular fluorine.

Pharmaceutically acceptable salts of the compounds of the invention include acid addition salts with inorganic, e.g. nitric, hydrochloric, hydrobromic, sulfuric, perchloric and phosphoric acids or organic, e.g. acetic, trifluoroacetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium, bases or with organic bases, e.g. acyclic or cyclic amines, preferably triethylamine or piperidine.

As stated above, the present invention also includes within its scope pharmaceutically acceptable bio-precursors (otherwise known as pro-drugs) of the compounds of formula (I), i.e. compounds which have a different formula to formula (I) above but which, nevertheless, upon administration to a human being are converted directly or indirectly in vivo into a compound of formula (I).

Preferred compounds of the invention are the compounds of formula (I), wherein

A is benzene, 5,6,7,8-tetrahydronaphthalene, quinoline, indole or 7-azaindole;

$R_1$ is —H, —NH$_2$, —COOH, —CN, —SO$_3$H, —SO$_2$NH$_2$,

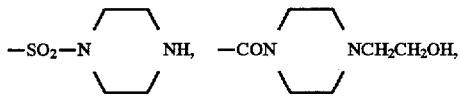

—COOMe, —N(CH$_2$CH$_2$OH)$_2$, —NHCH$_2$CHOHCH$_2$OH, —NHCONH$_2$, —NHC (NH₂)=NH, —NHCOCHOHCH₂OH,

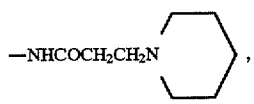

—NHSO₂Me, —OCH₂CHOHCH₂OH,
—OOCCH₂OH, —OOCCHOHCH₂OH, —OH,
—OMe, —OPO(OH)₂, —CH₂NH₂, —C(NH₂)=NH,

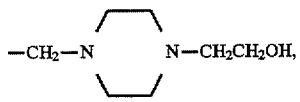

—CH₂OH, —OPO(OH)₂, —PO(OH)₂;

$R_2$ is $C_1$-$C_6$ alkyl or hydroxy;

$R_3$ is —H;

q is zero, 1 or 2;

and the azaoxindolylidene substituent is preferably linked to position 1 or 2 when A is naphthalene or 5,6,7,8-tetrahydronaphthalene, to position 4 or 5 when A is quinoline, to position 3 when A is indole or 7-azaindole, whereas the $R_1$ substituent is preferably linked to the other ring moiety when A is bicyclic, and the pharmaceutically acceptable salts thereof.

Examples of specific compounds of the invention are the following compounds, which, when appropriate may be either Z- or E-diastereomers or Z,E-mixtures of said diastereomers:

1) 3-[(3,5-di-tert-butyl-4-hydroxyphenyl)methylene]-7-azaoxindole;
2) 3-[(4-hydroxyphenyl)methylene]-7-azaoxindole;
3) 3-[4-(2,3-dihydroxypropoxy)phenylmethylene]-7-azaoxindole;
4) 3-[(4-methoxyphenyl)methylene]-7-azaoxindole;
5) 3-[(4-aminophenyl)methylene]-7-azaoxindole;
6) 3-[(4-diethanolaminophenyl)methylene]-7-azaoxindole;
7) 3-[(4-glyceroylamidophenyl)methylene]-7-azaoxindole;
8) 3-[4-(3-piperidinopropionylamino)phenyl)methylene]-7-azaoxindole;
9) 3-[(4-ureidophenyl)methylene]-7-azaoxindole;
10) 3-[(4-mesylaminophenyl)methylene]-7-azaoxindole;
11) 3-[(4-guanidinophenyl)methylene]-7-azaoxindole;
12) 3-[(4-sulfophenyl)methylene]-7-azaoxindole;
13) 3-[(4-N,N-piperazinylsulfamoylphenyl)methylene]-7-azaoxindole;
14) 3-[(4-sulfamoylphenyl)methylene]-7-azaoxindole;
15) 3-[(4-aminomethylphenyl)methylene]-7-azaoxindole;
16) 3-[(4-amidinophenyl)methylene]-7-azaoxindole;
17) 3-[(4-phosphonooxyphenyl)methylene]-7-azaoxindole;
18) 3-[(4-carboxyphenyl)methylene]-7-azaoxindole;
19) 3-[(4-carbomethoxyphenyl)methylene]-7-azaoxindole;
20) 3-[(4-hydroxymethylphenyl)methylene]-7-azaoxindole;
21) 3-[4-(2,3-dihydroxypropylamino)phenylmethylene]-7-azaoxindole;
22) 3-[(4-glycoloyloxyphenyl)methylene]-7-azaoxindole;
23) 3-[(4-phosphonophenyl)methylene]-7-azaoxindole;
24) 3-[(4-hydroxyethylpiperazin-1-ylmethyl)phenyl methylene]-7-azaoxindole;
25) 3-[4-(N,N-(4'-hydroxyethyl)piperazinylcarbamoyl)phenyl methylene]-7-azaoxindole;
26) 3-[4-sulfophenylmethylene]-7-azaoxindole sodium salt;
27) 3-[4-aminophenylmethylene]-7-azaoxindole hydrochloride;
28) 3-[4-aminophenylmethylene]-7-azaoxindole trifluoro-acetate;
29) 3-[(3-hydroxy-5,6,7,8-tetrahydronaphth-2-yl)methylene]-7-azaoxindole;
30) 3-[(1,4-dihydroxy-5,6,7,8-tetrahydronaphth-2-yl)methylene]-7-azaoxindole;
31) 3-[3-(2,3-dihydroxypropoxy)-5,6,7,8-tetrahydronaphth-2-yl)methylene]-7-azaoxindole;
32) 3-[(3-methoxy-5,6,7,8-tetrahydronaphth-2-yl)methylene]-azaoxindole;
33) 3-[(4-amino-5,6,7,8-tetrahydronaphth-1-yl)methylene]-7-azaoxindole;
34) 3-[(4-diethanolamino-5,6,7,8-tetrahydronaphth-1-yl)methylene]-7-azaoxindole;
35) 3-[(4-glyceroylamido-5,6,7,8-tetrahydronaphth-1-yl)methylene]-7-azaoxindole;
36) 3-[4-(3-piperidinopropionylamino)-5,6,7,8-tetrahydro naphth-1-yl)methylene]-7-azaoxindole;
37) 3-[(4-ureido-5,6,7,8-tetrahydronaphth-1-yl)methylene]7-azaoxindole;
38) 3-[(4-mesylamino-5,6,7,8-tetrahydronaphth-1-yl)methylene]-7-azaoxindole;
39) 3-[(4-guanidino-5,6,7,8-tetrahydronaphth-1-yl)methylene]-7-azaoxindole;
40) 3-[(4-sulfo-5,6,7,8-tetrahydronaphth-1-yl)methylene]-7-azaoxindole;
41) 3-[(4-N,N-piperazinylsulfamoyl-5,6,7,8-tetrahydronaphth-th-1-yl)methylene]-7-azaoxindole;
42) 3-[(4-sulfamoyl-5,6,7,8-tetrahydronaphth-1-yl)methylene]-7-azaoxindole;
43) 3-[(4-aminomethyl-5,6,7,8-tetrahydronaphth-1-yl)methylene]-7-azaoxindole;
44) 3-[(4-amidino-5,6,7,8-tetrahydronaphth-1-yl)methylene]-7-azaoxindole;
45) 3-[(4-phosphono-5,6,7,8-tetrahydronaphth-1-yl)methylene]-7-azaoxindole;
46) 3-[(4-carboxy-5,6,7,8-tetrahydronaphth-1-yl)methylene]-7-azaoxindole;
47) 3-[(4-carbomethoxy-5,6,7,8-tetrahydronaphth-1-yl)methylene]-7-azaoxindole;
48) 3-[(4-quinolyl)methylene]-7-azaoxindole;
49) 3-[(8-hydroxy-5-quinolyl)methylene]-7-azaoxindole;
50) 3-[(8-sulfo-5-quinolyl)methylene]-7-azaoxindole;
51) 3-[(8-sulfamoyl-5-quinolyl)methylene]-7-azaoxindole;
52) 3-[(8-aminomethyl-5-quinolyl)methylene]-7-azaoxindole;
53) 3-[(2-methyl-3-indolyl)methylene]-7-azaoxindole;
54) 3-[(3-indolyl)methylene]-7-azaoxindole;
55) 3-[(5-hydroxy-3-indolyl)methylene]-7-azaoxindole;
56) 3-[(5-methoxy-3-indolyl)methylene]-7-azaoxindole;

57) 3-[(5-amino-3-indolyl)methylene]-7-azaoxindole;

58) 3-[(5-diethanolamino-3-indolyl)methylene]-7-azaoxindole;

59) 3-[(5-glyceroylamido-3-indolyl)methylene]-7-azaoxindole;

60) 3-[(5-(3-piperidinopropionylamino)-3-indolyl) methylene]-7-azaoxindole;

61) -3-[(5-ureido-3-indolyl)methylene]-7-azaoxindole;

62) 3-[(5-mesylamino-3-indolyl)methylene]-7-azaoxindole;

63) 3-[(5-guanidino-3-indolyl)methylene]-7-azaoxindole;

64) 3-[(5-sulfo-3-indolyl)methylene]-7-azaoxindole;

65) 3-[(5-N,N-piperazinylsulfamoyl-3-indolyl) methylene]-7-azaoxindole;

66) 3-[(5-sulfamoyl-3-indolyl)methylene]-7-azaoxindole;

67) 3-[(5-aminomethyl-3-indolyl)methylene]-7-azaoxindole;

68) 3-[(5-amidino-3-indolyl)methylene]-7-azaoxindole;

69) 3-[(5-phosphono-3-indolyl)methylene]-7-azaoxindole;

70) 3-[(5-carboxy-3-indolyl)methylene]-7-azaoxindole;

71) 3-[(5-carbomethoxy-3-indolyl)methylene]-7-azaoxindole;

72) 3-[(7-azaindol-3-yl)methylene]-7-azaoxindole;

73) 3-[(4-hydroxy-7-azaindol-3-yl)methylene]-7-azaoxindole;

74) 3-[(4-amino-7-azaindol-3-yl)methylene]-7-azaoxindole;

75) 3-[(4-(3-piperidinopropionylamino)) -7-azaindol-3-yl) methylene]-7-azaoxindole;

76) 3-[(4-ureido-7-azaindol-3-yl)methylene]-7-azaoxindole;

77) 3-[(4-sulfo-7-azaindol-3-yl)methylene]-7-azaoxindole;

78) 3-[(4-sulfamoyl-7-azaindol-3-yl)methylene]-7-azaoxindole;

79) 3-[(4-amidino-7-azaindol-3-yl)methylene]-7-azaoxindole;

80) 3-[(4-carboxy-7-azaindol-3-yl)methylene]-7-azaoxindole;

and the pharmaceutically acceptable salts of the above listed compounds.

The compounds of the invention, and the pharmaceutically acceptable salts thereof, can be obtained by a process comprising:

a) condensation of an aldehyde of formula (II)

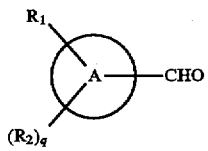

wherein A, $R_1$, $R_2$ and q are as defined above, with a compound of formula (III)

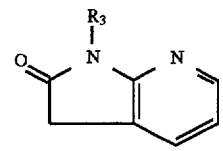

wherein $R_3$ is as defined above; or b) N-alkylation of a compound of formula (IV)

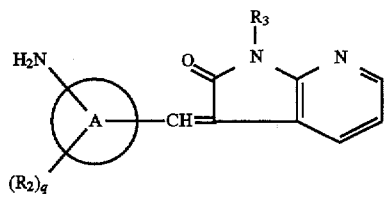

wherein A, $R_2$, $R_3$ and q are as defined above, thus obtaining a compound of formula (I), wherein $R_1$ is $-N(CH_2CH_2OH)_2$ or $-NHCH_2(CHOH)_nCH_2OH$ and A, $R_2$, $R_3$ and q are as defined above; or c) N-acetylation of a compound of formula (IV), wherein A, $R_2$, $R_3$ and q are as defined above, thus obtaining a compound of formula (I) wherein $R_1$ is $-NHCO(CHOH)_nCH_2OH$ or

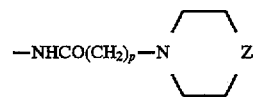

and A, $R_2$, $R_3$, n, p, q and Z are as defined above; or d) N-sulfonylation of a compound of formula (IV) wherein A, $R_2$, $R_3$ and q are as defined above, thus obtaining a compound of formula (I) wherein $R_1$ is $-NHSO_2R_9$ and A, $R_2$, $R_3$, $R_9$ and q are as defined above; or e) N-amidination of a compound of formula (IV) wherein A, $R_2$, $R_3$ and q are as defined above, thus obtaining a compound of formula (i) wherein $R_1$ is $-NHC(NH_2)=NH$ and A, $R_2$, $R_3$ and q are as defined above; or f) N-carbamoylation of a compound of formula (IV) wherein A, $R_2$, $R_3$ and q are as defined above, thus obtaining a compound of formula (I) wherein $R_1$ is $-NHCONH_2$ and A, $R_2$, $R_3$ and q are as defined above; or g) O-alkylation of a compound of formula (V)

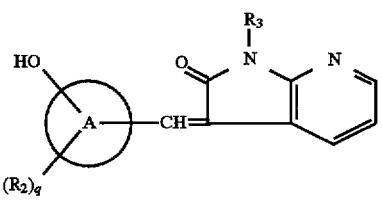

wherein A, $R_2$, $R_3$ and q are as defined above, thus obtaining a compound of formula (I) wherein $R_1$ is $-OCH_2(CHOH)_nCH_2OH$ or $-OR_{10}$ in which $R_{10}$ is $C_1-C_6$ alkyl and A, $R_2$, $R_3$ and q are as defined above; or h) O-acylation of a compound of formula (V) wherein A, $R_2$, $R_3$ and q are as defined above, thus obtaining a compound of formula (I) wherein $R_1$ is $-OOC(CHOH)_nCH_2OH$ or $-OR_{10}$ in which $R_{10}$ is $C_2-C_6$ alkanoyl and A, $R_2$, $R_3$ and q are as defined above; or i) O-phosphorylation of a compound of formula (V) wherein A, $R_2$, $R_3$ and q are as defined above, thus obtaining a compound of formula (I) wherein $R_1$ is —OPO(OH)$_2$ and A, $R_2$, $R_3$ and q are as defined above; or k) esterification of a compound of formula (VI)

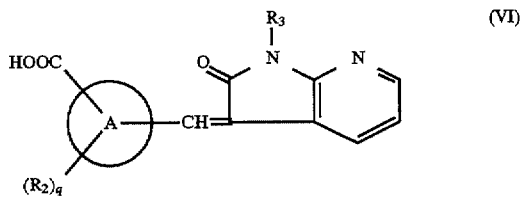

wherein A, $R_2$, $R_3$ and q are as defined above, thus obtaining a compound of formula (I) wherein $R_1$ is —COOR$_6$ and A, $R_2$, $R_3$ and q are as defined above; or l) ammonia addition of a compound of formula (VII)

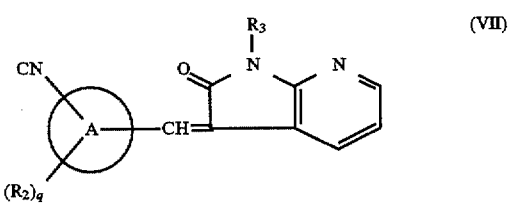

wherein A, $R_2$, $R_3$ and q are as defined above, thus obtaining a compound of formula (I) wherein $R_1$ is —C(NH$_2$)=NH and A, $R_2$, $R_3$ and q are as defined above; or m) amination of a compound of formula (VIII)

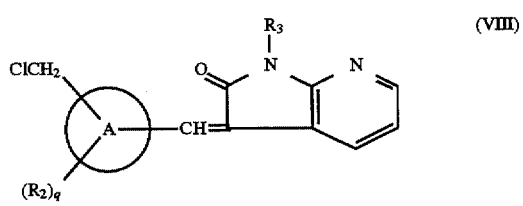

wherein A, $R_2$, $R_3$ and q are as defined above, thus obtaining a compound of formula (I) wherein $R_1$ is —CH$_2$NH$_2$ or

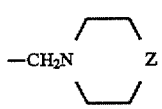

and A, $R_2$, $R_3$ and q are as defined above;

and/or conversion of a compound of formula (I) into another compound of formula (I) and/or optional salification of a compound of formula (I) or conversion of a salt into the corresponding free compound of formula (I) and/or, if desired, separation of a mixture of isomers into the single isomers.

The condensation of a compound of formula (II) with a compound of formula (III) according to process step a) may be carried out using known methods, e.g. under the condition of the Knoevenagel reaction as described e.g. by G. Jones in Organic Reactions 15, 204 (1967). Suitable catalysts are organic bases such as pyridine, piperidine or diethylamine.

The condensation may be performed in an inert organic solvent e.g. pyridine, ethanol, methanol, benzene or dioxane at temperatures ranging from about 0° C. to 100° C. Preferably the reaction is carried out in warm ethanol solution in the presence of piperidine catalyst.

The N-alkylation according to process step b) may be carried out according to known methods, e.g. as described in Houben Weyl, "Methoden der Organischen Chemie", Vol. XI/I., page 311 (1957). Thus, in order to obtain compounds of formula (I) wherein $R_1$ is —N(CH$_2$CH$_2$OH)$_2$, the aromatic amine is reacted with ethylene oxide in water, alcoholic or hydroalcoholic solution at temperatures from e.g. 0° C. to 100° C. Preferably the reaction is carried out in hydroalcoholic suspension at about 70°–80° C. by introducing ethylene oxide gas. On the other hand the N-alkylation according to process step b) in order to obtain compounds of formula (I) wherein $R_1$ and/or $R_3$ is —NHCH$_2$(CHOH)$_n$CH$_2$OH can be carried out by reductive amination, i.e. by condensation with an aldehyde of formula CH$_2$OH(CHOH)$_n$CHO in the presence of a reducing agent, e.g. as described by Tietze and Eiche in "Reactions and Synthesis in the Organic Chemistry Laboratory" (1988) at page 77. Thus, to the alcoholic solution of the aromatic amine and the aldehyde is added portionwise sodium cyanoborohydride at temperature ranging from 0° C. to reflux temperature.

The N-acylation according to process step c) may be carried out by known methods, e.g. as described in Houben-Weyl, Vol. E5, part II, page 960 (1985). Thus, the aromatic amine is reacted with the corresponding carboxylic acid of formula CH$_2$OH(CHOH)$_n$COOH or

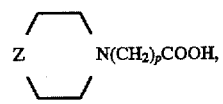

wherein Z, p and n are as defined above by using a condensing agent, such as dicyclohexylcarbodiimide (DCCD). Preferably equimolar amounts of amine, carboxylic acid and dicyclohexylcarbodiimide are used in an inert solvent such as THF or benzene at temperatures from about 0° C. to 50° C.

The N-sulfonylation according to process step d) may be carried out by known methods, e.g. as described in Houben-Weyl, Vol. IX, page 609 (1955). Thus, equimolar amounts of aromatic amine and sulphochloride of general formula $R^9$—SO$_2$—Cl are reacted in pyridine solution at temperatures from, e.g. 10° C. to 50° C.

The N-amidination according to process step e) may be carried out, e.g., as described by P. D. Davis et al. in J. Med. Chem. 1992, 35, 994. Thus, the aromatic amine is treated with about 1.5 molequivalents of 3,5-dimethylpyrazole-1-carboxamidine in refluxing ethanol in the presence of about 1 molequivalents of NaHCO$_3$.

The N-carbamoylation according to process step f) may be carried out, e.g., as described in Houben-Weyl, Vol. E4, page 362 (1983). Thus the aromatic amine salt, preferably the hydrochloride salt, is reacted with an alkali metal cyanate, preferably NaOCN or KOCN, in aqueous or hydroalcoholic solution at temperature ranging, e.g., from about 50° to about 100°.

The O-alkylation according to process step g) may be carried out, e.g., as described in Houben-Weyl, Vol. VI/3, page 54 (1965). Thus the phenol is first transformed into an alkali metal phenolate by treatment with an alkali metal alcoholate or hydroxide or amide. Then the phenolate is reacted with a halogenide of a general formula XCH$_2$(CHOH)$_n$CH$_2$OH (wherein X is chlorine or bromine) in an inert solvent such as benzene or THF at temperature ranging from room to reflux temperature.

Preferably the reaction is carried out in benzene solution by reacting the phenol first with a stoichiometric amount of NaNH$_2$ at room temperature and then with an excess of halogenide at reflux temperature.

The O-acylation according to process step h) may be carried out by known methods, e.g., as described in Houben- Weyl, Vol. VIII, page 543 (1952). Thus, the phenol is reacted with the acid halide of general formula $CH_2OH(CHOH)_nCOCl$ the presence of an organic base such as pyridine or triethylamine an temperatures ranging, e.g., from about to about 50° C. Aternatively, the phenol is reacted with the acid $CH_2OH(CHOH)_nCOOH$ in the presence of a condensing agent such as dicyclohexylcarbodiimide (DCCD). Preferably equimolar amounts of phenol and DCCD are used and the reaction is conducted in an inert solvent such as THF or benzene at temperatures from about 0° C. to about 50° C.

The O-phosphorylation according to process step i) maybe carried out by known methods, e.g., as described in Houben Weyl, Vol. XII/2, page 143 (1962). Thus, the phenol is reacted with the phosphoric acid or a derivative thereof water or hydroalcoholic solution at temperature ranging from room to reflux temperature. Preferably, the reaction is carried out in polyphosphoric acid (mixture of phosphoric acid and $P_2O_5$) which acts as reactant and solvent at temperature ranging from about 50° C. to about 100° C.

The esterification according to process step k) may be carried out by well known methods, e.g., as described in Houben-Weyl, Vol. VIII, page 508 (1952). Thus, the mixture of acid and alcohol, dissolved in an inert solvent such as benzene or chloroform, is heated to reflux in the presence of a mineral acid such as $H_2SO_4$. Preferably, the water formed is removed by azeotropic distillation in a Dean-Stark condenser.

The nitril transformation according to process step l) may be carried out by known methods, e.g. as described in Houben-Weyl, Vol. 8, page 697 and 702 (1952). Thus, to the ether or chloroform solution of the nitril is added an equimolar amount of ethanol and the resulting solution is saturated with HCl gas. The resulting iminoether hydrochloride is then transformed into amidine by reaction with ammonia in absolute ethanol at room temperature.

The amination according to process step m) may be carried out by known methods, e.g. as described in Houben-Weyl, Vol. XI/1, page 24 (1957). Thus, a mixture of chloromethyl compound and piperazine compound is heated to a temperature from, e.g., about 50° C. to about 150° C. until the reaction is complete.

The optional salification of a compound of formula (I) as well as the conversion of a salt into the corresponding free compound and the separation of a mixture of isomers into the single isomers as well as the conversion of a compound of formula (I) into another compound of formula (I) may be carried out according to known methods.

For example, the amidation of a compound of formula (I), wherein $R_1$ is —$SO_3H$, so as to obtain a compound of formula (I), wherein $R_1$ is —$SO_2NHR_5$ or

may be carried out by known methods, e.g., as described above at process step d).

The conversion of a compound of formula (I) in which $R_1$ is —$SO_3H$ into the corresponding compound of formula (I) wherein $R_1$ is —$SO_3R_4$ may be carried out by known esterification methods, e.g. as described above at process step k).

The conversion of a compound of formula (I) in which $R_1$ is —$CH_2NH_2$ into the corresponding compound of formula (I) wherein $R_1$ is —$CH_2NH$—$C(NH_2)$=$NH$ may be carried out by known amidination methods, e.g. as described above at process step e).

The esterification of a compound of formula (I) wherein $R_1$ is —$CH_2OH$ in order to obtain a compound of formula (I) wherein $R_1$ is —$CH_2OOC(CHOH)_nCH_2OH$ may be carried out by known amidination methods, e.g. as described above at process step k).

The conversion of a compound of formula (I) in which R is —$CH_2OH$ into the corresponding compound of formula (I) wherein $R_1$ is —$CH_2OPO(OH)_2$ may be carried out by known amidination methods, e.g. as described above at process step i).

The conversion of a compound of formula (I) in which $R_1$ is —$COOR_6$ and wherein $R_6$ is preferably methyl into the corresponding compound of formula (I) wherein $R_1$ is

may be carried out by aminolysis, e.g. as described in Houben-Weyl, vol. E5, page 983 (1985). Preferably a mixture of the carbomethoxy compound and the amine compound of formula

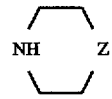

is heated to reflux and the formed methanol is continuously removed by distillation.

The optional salification of a compound of formula (I) as well as the conversion of a salt into the free compound and the separation of a mixture of isomers into the single isomers may be carried out by conventional methods. For example, the separation of a mixture of geometric isomers, e.g. cis- and trans-isomers, may be carried out by fractional crystallization from a suitable solvent or by chromatography, either column chromatography or high pressure liquid chromatography.

The compounds of formula (II) may be obtained according to known methods from compounds of formula (IX)

wherein A, $R_1$, $R_2$ and q are as defined above.

For example the 3-formylindole derivative of formula (II) can be obtained from an indole derivative of formula (IX) wherein A is indole and $R_1$, $R_2$ and q are as defined above, by formylation with N-methylformanilide and phosphorous oxychloride according to the well known Vilsmeyer-Haak method (for a review see W. G. Jackson et al. in J. Am. Chem. Soc. 1981, 103, 533). The 2-formyl-indole derivatives are obtained when the 3-position is occupied.

The 3-formyl-7-azaindole derivatives of formula (II) wherein A is 7-azaoxindole and $R_1$, $R_2$ and q are as defined above may be obtained by using the Vilsmeyer-Haak method as described above.

Moreover, phenolic compounds of formula (II) wherein A is benzene, naphthalene or 5,6,7,8-tetrahydronaphthalene may be obtained from the corresponding phenolic compounds of formula IIX) according to the well known method of Reimer-Tiemann by reaction with chloroform and alkali hydroxides in an aqueous or hydroalcoholic solution.

The compounds of formula (III) are known or may be obtained by known methods from known compounds. E.g. according to Marfat and Carta (Tetrahedron Letters, 1987, 28, 4027) the parent compound is obtained by brominating indole with pyridinium bromide perbromide to give 3,3-dibromo-7-azaoxindole which is then reduced to 7-azaoxindole with zinc in acetic acid.

A compound of formula IV), (V), (VI), (VII) or (VIII) that is a compound of formula (I) wherein $R_1$ is, respectively, —$NH_2$, —OH, —COOH, —CN or —$CH_2Cl$, may be obtained by condensation of a compound of formula (II) wherein $R_1$ is —$NH_2$, —OH, —COOH, —CN or —$CH_2Cl$ respectively, and $R_2$ and A are as defined above, with a compound of formula (III) according to process step a).

When in the new compounds of the present invention and in the intermediate products used for their preparation groups are present which need to be protected before submitting them to the hereabove illustrated reactions, they may be protected before the reaction takes place and then deprotected at the end of the reaction, according to well known methods in organic chemistry.

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence, the compounds according to the present invention can be useful in the treatment of pathological proliferation disorders in mammals, including humans. Typical examples of such disorders are tumors, including leukemia, and psoriasis. The compounds of the invention can also be useful in inhibiting the development of the atheromatous plaque and in the control of angiogenesis and as anti-metastatic agents. Recent studies on the molecular basis of the neoplastic transformation have identified a family of genes, designed oncogenes, whose aberrant expression causes tumorigenesis. For example, the RNA tumor viruses possess such an oncogene sequence whose expression determines neoplastic conversion of infected cells. Several of their oncogene-encoded proteins, such as $pp60^{v-src}$, $p70^{gag-yes}$, $p130^{gag-fps}$ and $p70^{gag-fgr}$ display protein tyrosine kinase activity, that is they catalyze the transfer of the gamma-phosphate from adenosine triphosphate (ATP) to tyrosine residues in protein substrate. In normal cells, several growth factor receptots, for example the receptors for PDGF, EGF, α-TGF and insulin, display tyrosine kinase activity. Binding of the growth factor (GF) activates the receptors tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinase can be useful in investigating the mechanism of cancerogenesis, cell proliferation and differentiations and it can be effective in the prevention and chemotherapy of cancer and in other pathological proliferative conditions, for instance as mentioned above.

The tyrosine specific protein kinase activity of the compounds of the invention is shown, e.g., by the fact that they are active in the in-vitro and in-vivo test described herebelow.

In-Vitro Assay
p45 v-abl Kinase Purification

The enzyme used in our tests was the p45 v-abl tyrosine kinase which represents the catalytic domain of the Abelson tyrosine kinase (isolated form the Abelson murine leukemia virus). The p45 v-abl kinase was produced and isolated as described by Wang at al. in J. Biol. Chem. 260, 64 (1985) and by Ferguson et al. in J. Biol. Chem. 260, 3652 (1985) and in Biochem. J. 257, 321 (1989).

p45 v-abl Kinase Assay (Val$^5$)-Angiotensin II phosphorylation was performed by incubation with 40 ng of purified abl-kinase and ($\gamma^{32}$-p)ATP, in 50 µl of buffer containing Tris-Hcl 25 mM, pH 8.0. $MgCl_2$ 10 mM and dithiothreitol 0.1 mM (kinase buffer). The reaction mixture was incubated for the indicated time at 30° C. and the reaction stopped by adding 50 µl of 5% trichloroacetic acid. After a brief incubation on ice, tubes were centrifuged. The supernatants were spotted on phosphocellulose paper squares (Whatman P-81) and washed extensively in acetic acid. The radioactivity bound to dried phosphocellulose squares was measured in a liquid scintillation counter. $IC_{50}$ values were calculated from triplicated determinations of each experimental point. Each inhibitor was tested at concentrations ranging from 0 to 400 µg in the presence of fixed concentrations of peptide (2 mM) and ATP (50 µM).

In-Vivo Assay
K562 Cell Growth Inhibition Assay

K562 cells, a human myelogenous leukemia cell line, were seeded into a 24 wells tissue culture plate (Falcon 3047) (10000/well) in the presence of increasing concentrations of the compounds. After 72 h, cells were harvested and were counted using a cell counter (Coulter Counter-ZM). The percent of inhibition was evaluated in respect to the untreated control cells.

The inhibitory activity data for a representative group of compounds according to the present invention, obtained both in the in-vitro p45 v-abl kinase assay and in the in vivo human chronic myeloid leukemia K562 cell growth inhibition assay described above, are set out in the following Table I.

TABLE I

| Compound | $IC_{50}$ (µM) | |
| --- | --- | --- |
|  | v-abl | K562 |
| 3-[(7-azaindol-3-yl)methylene]-7-azaoxindole | 1.04 | 3.89 |
| 3-[(1,4-dihydroxy-5,6,7,8-tetrahydronaphth-2-yl)methylene]-7-azaoxindole | 2.14 | 2.36 |
| 3-[(5-methoxy-3-indolyl)methylene]-7-azaoxindole | 0.03 | 3.21 |
| 3-[(2-methyl-3-indolyl)methylene]-7-azaoxindole | 0.04 | 2.61 |

In view of their high activity and low toxicity, the compounds of the invention can be used safely in medicine. For example, the approximate acute toxicity ($LD_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar or film-coated tablets, liquid solutions or suspensions; rectally, in the form of suppositories; parenterally, e.g. intramuscularly, or by intravenous injection or infusion; or topically. The dosage depends on the age, weight, condition of the patient and administration route; for example, the dosage adopted for oral administration to adult humans may range from about 10 to about 150–200 mg per dose, from 1 to 5 times daily. Of course, these dosage regimens may be adjusted to provide the optimal therapeutic response.

The invention includes pharmaceutical compositions comprising a compound of formula (I) or pharmaceutically acceptable salt thereof in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral form may contain, together with the active compound, diluents, e.g., lactose, dextrose, saccharose, cellulose, corn starch or potato starch; lubricant, e.g. silica, talc, stearic acid, magnesium or calcium stearate, and/or polyethylene glycols; binding agents, e.g. starches, arabic gums, gelatin, methylcellulose, carboxymethylcellulose or polyvynil pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be e.g. syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

The solutions for intravenous injections or infusion may contain as carrier, for example, sterile water or, preferable, they may be in the form of sterile aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin. Compositions for topical application, e.g. creams, lotions, or pastes, can be prepared by admixing the active ingredient with a conventional oleaginous or emulsifying excipient.

A further object of the present invention is a combined method of treatment of cancer in mammals, including humans, in need of such treatment, said method comprising administering:

1) a compound of formula (I), or a pharmaceutically acceptable salt thereof, and 2) an additional antitumor agent, in amounts and close enough together in time sufficient to produce a therapeutically useful effect.

Object of the present invention is also to provide products containing a compound of formula (I), or a pharmaceutically acceptable salt, and an additional antitumor agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice. Antitumor agents that can be formulated with a compound of the invention or alternatively, can be administered in a combined method of treatment, can be, e.g., doxorubicin, daunomycin, epirubicin, idarubicin, etoposide, fluorouracil, melphalan, cyclophosphamide, bleomycin, vinblastine and mitomycin or a mixture of two or more thereof.

The compounds of the invention can therefore be used in a treatment to ameliorate a cancer. They may be administered to a patient suffering from a cancer treatable with an antitumor agent, for example and anthracycline glycoside such as doxorubicin, daunomycin, epirubicin or idarubicin as mentioned above, together with the antitumor agent. A compound of the invention and an antitumor agent such e.g. as an anthracycline glycoside can be administered to improve the condition of a patient having a leukemia such as myeloblastic leukaemia, lymphoma, sarcoma, neuroblastoma, Wilm's tumor or malignant neoplasm of the bladder, breast, lung or thyroid.

The following examples illustrate but do not limit the invention:

EXAMPLE 1

3-[(3,5-di-t-butyl-4-hydroxyphenyl)methylene]7-azaoindole

A solution of 3,5-di-t-butyl-4-hydroxybenzaldeyde (2.343 g, 10 mmol), 7-azaoxindole (1.341 g, 10 mmol) and piperidine (0.255 g, 3 mmol) in absolute ethanol (50 ml) has heated for 3 h at reflux. The reaction mixture was chilled to 5°–10° C., the precipitate filtered, the residue washed with ice-cold ethanol and dried under vacuum. Almost pure title compound was so obtained in about 80% yield (0.280 g). Compound of higher purity were obtained by crystallization from ethanol.

$C_{22}H_{26}N_2O_2$ calcd: C 75.40 H 7.50 N 7.99 found: C 75.35 H 7.52 N 7.85

MS m/z 350

NMR E-isomer (DMSO) δ 1.40 (s, 3H), 6.9–7.0 (m, 1H), 7,52 (s, 1H), 7.70 (s, 1H), 7.71 (bs, 1H), 7.93 (dd, J=1.7 and 8.5 Hz, 1H), 8.07 (dd, J=1.7 and 5.1 Hz, 1H), 11.12 (s, 1H)

According to the above described procedure and starting from the appropriate compound of formula (II) and of formula (III), one can prepare the following compounds as single E- or Z-isomers, as well as their E,Z-mixtures:

3-[(1,4-dihydroxy-5,6,7,8-tetrahydronaphth-2-yl)methylene]-7-azaoxindole $C_{18}H_{16}N_2O_3$ calcd: C 70.12 H 5.23 N 9.08 found: C 70.05 H 5.15 N 9.01

MS m/z 308

NMR E-isomer (DMSO) δ 1.67 (m, 4H), 6.91 (s, 1H), 6.92 (dd, J=5.1 and 7.6 Hz, 1H), 7.84 (s, 1H), 7.91 (dd, J=7.6 and 1.5 Hz, 1H), 8.06 (dd, J=5.1 and 1.5 Hz, 1H), 8.4 (bs, 3H), 9.01 (s, 1H), 11.10 (s, 1H)

3-[(3-hydroxy-5,6,7,8-tetrahydronaphth-2-yl)methylene]-7-azaoxindole $C_{18}H_{16}N_2O_2$ calcd: C 73.95 H 5.52 N 9.58 found: C 73.66 H 5.55 N 9.45

MS m/z 292

3-[(4-quinolyl)methylene]-7-azaoxindole

C₁₇H₁₁N₃O calcd: C 74.71 H 4.06 N 15.38 found: C 71.65 H 3.95 N 15.42

MS m/z 275

3-[(2-methyl-3-indolyl)methylene]-7-azaoxindole

C₁₇H₁₃N₃O calcd: C 74.17 H 4.76 N 15.26 found: C 74.15 H 4.66 N 15.30

MS m/z 275

NMR Z-isomer (DMSO) δ 6.79 (dd, J=7.5 and 5.0 Hz, 1H), 6.86 (dd, J=7.5 and 1.8 Hz, 1H), 6.9–7.5 (m, 4H), 7.94 (s, 1H), 7.99 (dd, J=1.8 and 5.0 Hz, 1H), 11.0 (bs, 1H), 12.0 (bs, 1H)

3-[(3-indolyl)methylene]-7-azaoxindole

C₁₆H₁₁N₃O calcd: C 73.55 H 4.24 N 16.08 found: C 73.48 H 4.19 N 15.55

MS m/z 261

NMR Z-isomer (DMSO) δ 7.00 (dd, J=5.2 and 7.4 Hz, 1H), 7.24 (m, 2H), 7.52 (m, 1H), 8.01 (dd, J=5.2 and 1.4 Hz, 1H), 8.1–8.3 (m, 3H), 9.43 (bs, 1H), 11.1 (bs, 1H), 12.1 (bs, 1H)

3-[(5-methoxy-3-indolyl)methylene]-7-azaoxindole

C₁₇H₁₃N₃O₂ calcd: C 70.09 H 4.50 N 14.42 found: C 70.01 H 4.45 N 14.35

MS m/z 291

NMR Z-isomer (DMSO) δ 3.86 (s,3H), 6.86 (dd, J=2.4 and 8.7 Hz, 1H), 6.99 (dd, J=5.1 and 7.6 Hz, 1H), 7.40 (d, J=8.7 Hz, 1H), 7.71 (d, J=2.4 Hz, 1H), 8.00 (dd, J=5.1 and 1.5 Hz, 1H), 8.19 (dd, J=7.6 and 1.5 Hz, 1H), 8.21 (s, 1H), 9.32 (s, 1H), 11.0 (bs, 1H), 12.0 (s, 1H).

3-[(7-azaindol-3-yl)methylene]-7-azaoxindole

C₁₅H₁₀N₄O calcd: C 68.69 H 3.84 N 21.36 found: C 68.65 H 3.85 N 21.25

MS m/z 262

NMR Z-isomer (DMSO) δ 7.02 (dd, J=5.3 and 7.5 Hz, 1H), 7.29 (dd, J=4.5 and 7.9 Hz, 1H), 8.03 (dd, J=5.3 and 1.5 Hz, 1H), 8.16 (dd, J=7.5 and 1.5 Hz, 1H), 8.22 (s, 1H), 8.35 (dd, J=4.5 and 1.5 Hz, 1H), 8.58 (dd, J=7.9 and 1.5 Hz, 1 H), 9.49 (s, 1H), 11.14 (s, 1H), 12.6 (bs, 1H).

3-[(4-hydroxyphenyl)methylene]-7-azaoxindole;
3-[4-(2,3-dihydroxypropoxy)phenylmethylene]-7-azaoxindole;
3-[(4-methoxyphenyl)methylene]-7-azaoxindole;
3-[(4-aminophenyl)methylene]-7-azaoxindole;
3-[(4-diethanolaminophenyl)methylene]-7-azaoxindole;
3-[(4-glyceroylamidophenyl)methylene]-7-azaoxindole;
3-[4-(3-piperidinopropionylamino)phenyl)methylene]-7-azaoxindole;
3-[(4-ureidophenyl)methylene]-7-azaoxindole;
3-[(4-mesylaminophenyl)methylene]-7-azaoxindole;
3-[(4-guanidinophenyl)methylene]-7-azaoxindole;
3-[(4-sulfophenyl)methylene]-7-azaoxindole;
3-[(4-N,N-piperazinylsulfamoylphenyl)methylene]-7-azaoxindole;
3-[4-sulfamoylphenyl)methylene]-7-azaoxindole;
3-[4-aminomethylphenyl)methylene]-7-azaoxindole;
3-[4-amidinophenyl)methylene]-7-azaoxindole;
3-[4-phosphonooxyphenyl)methylene]-7-azaoxindole;
3-[4-carboxyphenyl)methylene]-7-azaoxindOle;
3-[4-carbomethoxyphenyl)methylene]-7-azaoxindole;
3-[4-hydroxymethylphenyl)methylene]-7-azaoxindole;
3-[4-(2,3-dihydroxypropylamino)phenylmethylene]-7-azaoxindol;
3-[(4-glycoloyloxyphenyl)methylene]-7-azaoxindole;
3-[(4-phosphonophenyl)methylene]-7-azaoxindole;
3-[(4-hydroxyethyl-1-piperazin-1-ylmethyl)phenylmethylene]-7-azaoxindole;
3-[4-(N,N-(4'-hydroxyethyl)piperazinylcarbamoyl)phenyl methylene]-7-azaoxindole;
3-[4-sulfophenylmethylene]-7-azaoxindole sodium salt;
3-[4-aminophenylmethylene]-7-azaoxindole hydrochloride;
3-[4-aminophenylmethylene]-7-azaoxindole trifluoroacetate;
3-[3-(2,3-dihydroxypropoxy)-5,6,7,8-tetrahydronaphth-2-yl)methylene]7-azaoxindole;
3-[(3-methoxy-5,6,7,8-tetrahydronaphth-2-yl)methylene]-7-azaoxindole;
3-[(4-amino-5,6,7,8-tetrahydronaphth-1-yl)methylene]-7-azaoxindole;
3-[(4-diethemolamino-5,6,7,8-tetrahydronaphth-1-yl)methylene]-7-azaoxindole;
3-[(4-glyceroylamino-5,6,7,8-tetrahydronaphth-1-yl)methylene]-7-azaoxindole;
3-[4-(3-piperidinopropionylamino)-5,6,7,8-tetrahydronaphth-1-yl) methylene]-7-azaoxindole;
3-[(4-ureido-5,6,7,8-tetrahydronaphth-1-yl)methylene]-7-azaoxindole;
3-[(4-mesylamino-5,6,7,8-tetrahydronaphth-1-yl) methylene]-7-azaoxindole;
3-[(4-guanidino-5,6,7,8-tetrahydronaphth-1-yl)methylene]-7-azaoxindole;
3-[(4-sulfo-5,6,7,8-tetrahydronaphth-1-yl)methylene]-7-azaoxindole;
3-[4-N,N-piperazinylsulfamoyl-5,6,7,8-tetrahydronaphth-1-yl) methylene]-7-azaoxindole;
3-[4-sulfamoyl-5,6,7,8-tetrahydronaphth-1-yl)methylene]-7-azaoxindole;
3-[4-aminomethyl-5,6,7,8-tetrahydronaphth-1-yl) methylene]-7-azaoxindole;
3-[4-amidino-5,6,7,8-tetrahydronaphth-1-yl)methylene]-7-azaoxindole;
3-[4-phosphono-5,6,7,8-tetrahydronaphth-1-yl)methylene]-7-azaoxindole;
3-[4-carboxy-5,6,7,8-tetrahydronaphth-1-yl)methylene]-7-azaoxindole;
3-[(4-carbomethoxy-5,6,7,8-tetrahydronaphth-1-yl)methylene]-7-azaoxindole;
3-[(8-hydroxy-5-quinolyl)methylene]-7-azaoxindole;
3-[8-sulfo-5-quinolyl)methylene]-7-azaoxindole;
3-[8-sulfamoyl-5-quinolyl)methylene]-7-azaoxindole;
3-[8-aminomethyl-5-quinolyl)methylene]-7-azaoxindole;
3-[5-hydroxy-3-indolyl)methylene]-7-azaoxindole;
3-[5-amino-3-indolyl)methylene]-7-azaoxindole;
3-[5-diethanolamino-3-indolyl)methylene]-7-azaoxindole;
3-[5-glyceroylamido-3-indolyl)methylene]-7-azaoxindole;
3-[5-(3-piperidinopropionylamino)-3-indolyl)methylene]-7-azaoxindole;
3-[(5-ureido-3-indolyl)methylene]-7-azaoxindole;
3-[(5-mesylamino-3-indolyl)methylene]-7-azaoxindole;
3-[(5-guanidino-3-indolyl)methylene]-7-azaoxindole;
3-[(5-sulfo-3-indolyl)methylene]-7-azaoxindole;
3-[(5-N,N-piperazinylsulfamoyl-3-indolyl)methylene]-7-azaoxindole;
3-[(5-sulfamoyl-3-indolyl)methylene]-7-azaoxindole;
3-[5-aminomethyl-3-indolyl)methylene]-7-azaoxindole;
3-[5-amidino-3-indolyl)methylene]-7-azaoxindole;

3-[5-phosphono-3-indolyl)methylene]-7-azaoxindole;
3-[5-carboxy-3-indolyl)methylene]-7-azaoxindole;
3-[5-carbomethoxy-3-indolyl)methylene]-7-azaoxindole;
3-[7-azaindol-3-yl)methylene]-7-azaoxindole;
3-[4-hydroxy-7-azaindol-3-yl)methylene]-7-azaoxindole;
3-[4-amino-7-azaindol-3-yl)methylene]-7-azaoxindole;
3-[4-(3-piperidinopropionylamino))-7-azaindol-3-yl)methylene]-7-azaoxindole;
3-[(4-ureido-7-azaindol-3-yl)methylene]-7-azaoxindole;
3-[(4-sulfo-7-azaindol-3-yl)methylene]-7-azaoxindole;
3-[(4-sulfamoyl-7-azaindol-3-yl)methylene]-7-azaoxindole;
3-[(4-amidino-7-azaindol-3-yl)methylene]-7-azaoxindole;
3-[(4-carboxy-7-azaindol-3-yl)methylene]-7-azaoxindole.

EXAMPLE 2

3-[4-(2,3-dihydroxypropylamino)phenylmethylene]-7-azaoxindole

To a stirred solution of 3-(4-aminobenzylidene)-7-azaindole (2.373 g, 10 mmol) in methanol (30 ml) was added anhydrous methylammonium chloride (0.60 g, 10 mmol). Then sodium cyanoborohydride (0.378 g, 6 mmol) was added in portions. Finally, glyceraldehyde (0.901 g, 10 mmol) was added portionwise over 30 min and the solution stirred at room temperature for 50 h. Ice cold 6N HCl was added until gas evolution (HCN) stopped and the pH of the solution was 2. The methanol was evaporated in vacuo and the remaining aqueous solution was washed with $CHCl_3$. Solid KOH was added until the pH was 12. Solid NaCl was added to saturation and the solution extracted twice with $CHCl_3$. The $CHCl_3$ extracts were washed with saturated NaCl solution, dried over $K_2CO_3$ and evaporated. The residue was chromatographed on silica gel using $CHCl_3$-MeOH mixtures as eluant. Thus pure title compound was obtained in about 60% yield.

$C_{17}H_{17}N_3O_3$ calcd: C 65.58 H 5.51 N 13.50 found: C 65.57 H 5.45 N 13.55

MS m/z 311

EXAMPLE 3

3-[(4-glyceroylamidophenyl)methylene]-7-azaoxindole

To a stirred solution of 3-(4-aminobenzylidene)-7-azaoxindole (2.373 g, 10 mmol) and glyceric acid (1.061 g, 10 mmol) in benzene (200 ml) was added dicyclohexyl carbodiimide (2.063 g, 10 mmol). The resulting suspension was stirred for 1 h at 50°–60° C. and then for 3 days at room temperature. Then the N,N'-dicyclohexylurea was filtered off, the filtrate evaporated and the residue chromatographed on silica gel using $CHCl_3$—MeOH mixtures as eluant. Thus pure title compound was obtained in about 50% yield.

$C_{17}H_{15}N_3O_4$ calcd: C 62.76 H 4.65 N 12.92 found: C 62.65 H 4.63 N 12.85

MS m/z 325

IR $cm^{-1}$: 3600–2500 (NH,OH), 1680 (CO), 1650 (CO), 1620 (amide)

EXAMPLE 4

3-[(4-mesylaminophenyl)methylene]-7-azaoxindole

To a stirred solution of 3-(4-aminobenzylidene)-7-azaoxindol (2.373 g, 10 mmol) in pyridine (10 ml) was added gradually mesylchloride (1.146 g, 10 mmol) at 0°–5° C. under cooling. The reaction mixture was stirred for about 5 h at 0°–5° C. and then for 15 h at room temperature. The mixture was poured onto an ice-water mixture, the precipitate filtered off, the residue washed thoroughly with water and then chromatographed on silica gel using $CHC_3$-MeOH mixtures as eluant. Thus pure title compound was obtained in about 70% yield.

$C_{15}H_{13}N_3O_3S$ calcd: C 57.13 H 4.15 N 13.32 S 10.17 found: C 57.05 H 4.08 N 13.25 S 10.05

MS m/z 315

IR $cm^{-1}$: 3600–3000 (NH), 1650 (CO), 1600, 1580 (C=C).

EXAMPLE 5

3-[(4-guanidinophenyl)methylene]-7-azaoxindole

A mixture of 3-(4-aminobenzylidene)-7-azaoxyindole (2.373 g, 10 mmol) and sodium bicarbonate (0.168 g, 2 mmol) in refluxing ethanol (100 ml) was treated with 3,5-dimethylpyrazole-1-carboxamidine nitrate (3.018 g, 15 mmol) for 20 h. The solvent was removed from the cooled solution, and the residue was chromatographed on silica gel with gradient elution (1 to 5% EtOH in $CHCl_3$) to afford pure title compound in about 50% yield.

$C_{17}H_{14}N_5O$ calcd: C 64.57 H 4.69 N 25.07 found: C 64.45 H 4.55 N 29.95

MS m/z 279

IR $cm^{-1}$: 3600–3100 (NH), 1680 (C=NH), 1655 (CONH), 1620, 1580 (C=C).

EXAMPLE 6

3-[(4-ureidophenyl)methylene]-7-azaoxindole

A mixture of 3-(4-aminobenzylidene)-7-azaoxindole (2.373 g, 10 mmol) in ice water (20 ml) are added 5N HCl (2 ml, 10 mmol under stirring. Then the mixture was heated to 70°–80° C., sodium cyanate (0.715 g, 11 mmol) was added portionwise and the stirring was continued for further 4 h at this temperature.

After cooling the raw product was extracted with $CHCl_3$, the organic layer washed to neutrality with saline solution, dried and evaporated in vacuo.

The residue was chromatographed on silica gel using $CHCl_3$—MeOH mixtures as eluant to give pure title compound in about 50% yield.

$C_{15}H_{12}N_4O_2$ calcd: C 64.28 H 4.32 N 19.99 found: C 64.30 H 4.25 N 19.81

MS m/z 280

IR $cm_{-1}$: 3600–3000 (NH), 1660 (CO), 1645 (CO), 1610, 1590 (C=C)

EXAMPLE 7

3-[4-(2,3-dihydroxypropoxyphenylmethylene]-7-azaoxindole

To a solution of 3-(4-hydroxybenzylidene)-7-azaoxindole (2.383 g, 10 mmol) in toluene (100 ml) was added portionwise under nitrogen NaH 80% (0.300 g, 10 mmol). After the salification was complete 3-chloro-1,2-propanediol (1.547 g, 14 mmol) was added and the mixture heated to reflux for 5 h.

After cooling water was added, the organic phase washed and evaporated to dryness. The residue was submitted to flash chromatography using $CHCl_3$—MeOH mixtures as eluant to give pure title compound in about 70% yield.

$C_{17}H_{16}N_2O_4$ calcd: C 65.38 H 5.16 N 8.99 found: C 65.25 H 5.05 N 8.85

MS m/z 312

IR cm$^{-1}$: 3600–2600 (NH, OH), 1660 (CO), 1610, 1580, (C=C).

EXAMPLE 8

3-[(4-glycoloyloxyphenyl)methylene]-7-azaoxindole

To a stirred solution of 3-(4-hydroxybenzylidene)-7-azaoxindole (2,383 g. 10 mmol) in pyridine (10 ml) was added gradually glycoloyl chloride (0.945 g, 10 mmol) at 0°–5° C. under cooling. The reaction mixture was stirred for about 4 h at 0°–5° C. and then for 15 h at room temperature. The mixture was poured onto an ice-water mixture, the precipitate filtered off, the residue washed thoroughly with water and then chromatographed on silica gel using CHCl$_3$—MeOH mixtures as eluant. Thus pure title compound was obtained in about 60% yield.

$C_{16}H_{12}N_2O_4$ calcd: C 64.86 H 4.08 N 9.45 found: C 64.81 H 3.98 N 9.25

MS m/z 296

IR cm$^{-1}$: 3600–2600 (NH, OH), 1740 (CO), 1660 (CO), 1620, 1580.

EXAMPLE 9

3-[(4-phosphonoxyphenyl)methylene]-7-azaoxindole

A mixture of 3-(4-hydroxybenzylidene)methylene]-7-azaoxindole (2.383 g, 10 mmol) and phosphoric acid 85% (13 g) and phosphorus pentoxide (10 g) was heated for 2 h at 60° C. The usual work up gave the title compound in about 50% yield.

$C_4H_{11}N_2O_5P$ calcd: C 52.84 H 3.48 N 8.80 P 9.73 found: C 52.79 H 3.45 N 8.75 P 9.65

MS m/z 318

EXAMPLE 10

3-[(4-carbomethoxyphenyl)methylene]-7-azaoxindole

A solution of 3-(4-carboxybenzylidene)-7-azaoxindole (2.663 g, 10 mmol), methanol (3.2 g, 0.1 mol) and H$_2$SO$_4$ 95% (1 g) in benzene (100 ml) was heated in a Soxhlet apparatus for 10 h. To dry the distillate continuously, the cap of the Soxhlet contained anhydrous MgSO$_4$. After cooling, water was added, the organic phase repeatedly washed with water and then evaporated under vacuum. Thus almost pure title compound was obtained in about 90% yield.

$C_{15}H_{12}N2_3O_3$ calcd: C 67.16 H 4.51 N 10.44 found: C 67.05 H 4.45 N 13.35

MS m/z 268

IR cm$^{-1}$: 3600–3200 (NH), 1720 (COOMe), 1660 (CO), 1620, 1600, 1580.

EXAMPLE 11

3-[(4-amidinophenyl)methylene]-7-azaoxindole hydrochloride

To a solution of 3-(4-cyanobenzylidene)-7-azaoxindole (2.473 g, 10 mmol) in anhydrous diethylether (100 ml) a stechiometric amount of ethanol (0.460 g, 10 mmol) was added and the solution was saturated with hydrogen chloride gas. The solution was kept overnight in the fridge in order to precipitate the iminoether hydrochloride salt. The precipitated aminoether hydrochloride was dissolved in ethanol (50 ml) to which was added an anhydrous alcoholic ammonia solution. Thereupon the solution was kept several days at room temperature and the precipitated little amount of NH$_4$Cl was filtered off. The solution was evaporated in vacuum, thus obtaining almost pure title compound.

$C_{15}H_{12}N_4O.HCl$ calcd: C 59.91 H 4.36 N 18.63 Cl 11.79 found: C 59.85 H 4.25 N 18.55 Cl 11.80

MS m/z 300

EXAMPLE 12

3-(4-hydroxyethyl-1-piperazinylmethyl) phenylmethylene]-7-azaoxindole

A mixture of 3-(4-chloromethylbenzylidene)-7-azaoxindole (2.707 g, 10 mmol) and 4-hydroxyethylpiperazine (2.604 g, 20 mmol) in 1N NaOH (20 ml, 20 mmol) was refluxed for 48 h. The cooled reaction mixture was extracted with ether, and the ether extract was shaken with diluted hydrochloric acid. The aqueous acid layer was made alkaline with potassium carbonate and extracted with ether. Addition of hydrogen chloride to the dried ether extract precipitated a crude hydrochloride which was crystallized twice from a mixture of methanol and ether.

$C_{21}H_{24}N_4O_2HCl$ calcd: C 62.91 H 6.29 N 13.98 Cl 8.84 found: C 62.85 H 6.15 N 13.85 Cl 8.75

MS m/z 400

EXAMPLE 13

3-[4-[N,N-(4-hydroxyethyl)piperazinylcarbamoyl) phenyl methylene]-7-azaoxindole

A mixture of 3-(4-carbomethoxybenzylidene)-7-azaoxindole (2.803 g, 10 mmol), 4-hydroxyethyl-piperazine (1.302 g, 10 mmol) and sodium mathoxide (0.540 g, 10 mmol) in benzene (50 ml) was heated to reflux for 10h. After cooling water was added cautiously, the organic phase was washed thoroughly with water and then evaporated under vacuum. The residue was submitted to column chromatography on silica gel using CHCl$_3$-MeOH mixtures as eluant. Thus pure title compound was obtained in about 60% yield.

$C_{21}H_{22}N_4O_3$ calcd: C 66.65 H 5.86 N 14.81 found: C 66.55 H 5.75 N 14.57

MS m/z 378

EXAMPLE 14

3-[4-sulfophenylmethylene]-7-azaoxindole sodium salt

To a solution of 3-(4-sulfobenzylidene)-7-azaoxindole (3.206 g, 10 mmol) in 1N NaOH (10 ml, 10 mmol) was added isopropanol (30 ml) and the mixture was chilled under stirring to 0°–5° C. The precipitated sodium salt was filtered, washed with ice-cooled isopropanol and dried under vacuum.

$C_{14}H_9N_2O_4SNa$ calcd: C 51.85 H 2.80 N 8.64 S 9.89 Na 7.09 found: C 51.75 H 2.75 N 8.60 S 9.81Na 6.95

MS m/z 324

EXAMPLE 15

3-4-aminophenylmethylene)-7-azaoxindole hydrochloride salt

To a solution of 3-(4-aminobezylidene-7-azaoxindole (2.373 g, 10 mmol) in ethanol (10 ml) was added 1N hydrochloridric acid (2 ml, 2 mmol) and the resulting mixture was evaporated to dryness under vacuum thus giving pure title compound in about 100% yield.

$C_{14}H_{11}N_3O \cdot HCl$ calcd: C 61.43 H 4.42 N 15.35 Cl 12.95 found: C 61.35 H 4.39 N 15.31 Cl 12.81

MS m/z 273

EXAMPLE 16

3-(4-aminophenylmethylene)-7-azaoxyindole trifluoroacetate salt

To a solution of 3-(4-aminobenzylidene)-7-azaoxindole (0.237 g, 1 mmol) in ethanol (10 ml) was added trifluoroacetic acid (0.114 g, 1 mmol and the solution was concentrated under vacuum to a small volume. Ether was added to precipitate the salt, the mixture was ice-cooled, the solid was filtered off, washed with cold ether and essicated under vacuum. Thus almost pure title compound was obtained in about 90% yield.

$C_{16}H_{12}F_3N_3O_3$ calcd: C 54.71 H 3.44 N 11.96 F 16.23 found: C 54.65 H 3.35 N 11.85 F 16.25

MS m/z 351

EXAMPLE 17

7-azaindol-3-carboxaledehyde

A solution of 7-azaindole (23.6 g, 0.20 mol) and hexamethylenetetramine (42 g, 0.30 mol) in 33% acetic acid (84 g, 1.4 mol and 168 ml $H_2O$) was refluxed for 6 h. The resulting clear yellow solution was diluted with water, and the product was allowed to crystallize in the refrigerator overnight. Recrystallization of the crude product from water gave almost pure title compound in 50% yield (14.9 g).

m.p. 216°–218° C.

$C_8H_6N_2O$ calcd: C 65.74 H 4.13 N 19.17 found: C 65.65 H 4.05 N 19.05

MS m/z 146

EXAMPLE 18

Tablets each weighing 0.150 g and containing 25 mg of the active substance, can be manufactured as follows: Composition (for 10,000 tablets):

| | |
|---|---|
| 3-[(3,5-di-t-butyl-4-hydroxyphenyl)methylen]-7-azaoxindole | 250 g |
| Lactose | 800 g |
| Corn starch | 415 g |
| Talc powder | 30 g |
| Magnesium stearate | 5 g |

The 3-[(3,5-di-t-butyl-4-hydroxyphenyl)methylen]-7-azaoxindole, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 19

Capsules, each dosed at 0.200 g and containing 20 mg of the active substance can be prepared. Composition for 500 capsules:

| | |
|---|---|
| 3-[(7-azaindol-3-yl)methylene]-7-azaoxindole | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of formula (I)

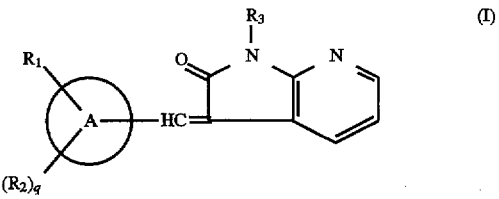

wherein

A is benzene, naphthalene, 5,6,7,8,-tetrahydronaphthalene, quinoline, isoquinoline, indole or 7-azaindole;

$R_1$ is —H, —CN, —$SO_3R_4$, —$SO_2NHR_5$,

—$COOR_6$, —$CONHCH_2(CHOH)_nCH_2OH$,

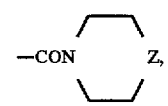

—$NR_7R_8$, —$N(CH_2CH_2OH)_2$, —$NHCH_2(CHOH)_2CH_2OH$, —$NHCONH_2$, —$NH$—$C(NH_2)$=$NH$, —$NHCO(CHOH)_nCH_2OH$,

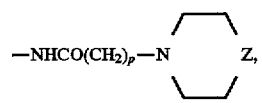

—$NHSO_2R_9$, —$OR_{10}$, —$OCH_2(CHOH)_nCH_2OH$, —$OOC(CHOH)_nCH_2OH$, —$OPO(OH)_2$, —$CH_2NH_2$, —$C(NH_2)$=$NH$, —$CH_2NHC(NH_2)$=$NH$,

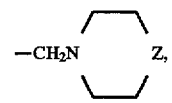

—$CH_2OH$, —$CH_2OOC(CHOH)_nCH_2OH$, —$CH_2OPO(OH)_2$ or —$PO(OH)_2$;

$R_2$ is $C_1$–$C_6$ alkyl, halogen, or hydroxy;

$R_3$ is —H or $C_1$–$C_6$ alkyl;

$R_4$ is —H, $C_1$–$C_6$ alkyl or —$CH_2(CHOH)_nCH_2OH$;

$R_5$ is —H, $C_1$–$C_6$ alkyl, —$CH_2(CHOH)_nCH_2OH$ or —$(CH_2)_mNMe_2$;

$R_6$ is —H, $C_1$–$C_6$ alkyl or —$CH_2(CHOH)_nCH_2OH$;

each of $R_7$ and $R_8$ independently is —H or $C_1$–$C_6$ alkyl;

$R_9$ is methyl or tolyl;

$R_{10}$ is —H, $C_1$–$C_6$ alkyl or $C_2$–$C_6$ alkanoyl;

Z is >$CH_2$, >O, >NH or >$NCH_2CH_2OH$;

n is zero or 1;

m is 2 or 3;

p is 1, or 3;

q is zero, 1 or 2;

and the pharmaceutically acceptable salt thereof.

2. A compound of formula (I) according to claim 1 wherein:

A is benzene, 5,6,7,8-tetrahydronaphthalene, quinoline, indole or 7-azaindole;

$R_1$ is —H, —$NH_2$, —COOH, —CN, —$SO_3H$, —$SO_2NH_2$,

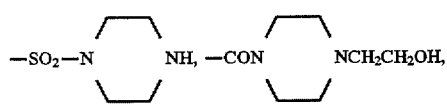

—COOMe, —$N(CH_2CH_2OH)_2$, —$NHCH_2(CHOH)CH_2OH$, —$NHCONH_2$, —$NHC(NH_2)=NH$, —$NHCO(CHOH)CH_2OH$,

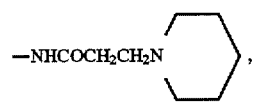

—$NHSO_2Me$, —$OCH_2(CHOH)CH_2OH$, —$OOCCH_2OH$, —$OOO(CHOH)CH_2OH$, —OH, —OMe, —$OPO(OH)_2$, —$CH_2NH_2$, —$C(NH_2)=NH$,

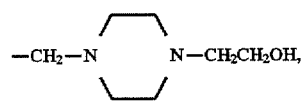

—$CH_2OH$, —$PO(OH)_2$;

$R_2$ is $C_1$–$C_6$ alkyl or hydroxy;

$R_3$ is —H;

q is zero, 1 or 2;

and the azaoxindolylidene substituent is linked to position 1 or 2 when A is naphthalene or 5,6,7,8-tetrahydronaphthalene, to position 4 or 5 when A is quinoline, to position 3 when A is indole or 7-azaindole, whereas the $R_1$ substituent is linked to the other ring moiety when A is bicyclic, and the pharmaceutically acceptable salts thereof.

3. A compound which, when appropriate, may be either a Z or an E-diasteromer or a Z,E-mixture of said diasteromers, selected from a group consisting of:

3-[(3,5-di-tert-butyl-4-hydroxyphenyl)methylene]-7-azaoxindole;

3-[(4-hydroxyphenyl)methylene]-7-azaoxindole;

3-[4-(2,3-dihydroxypropoxy)phenylmethylene]-7-azaoxindole;

3-[(4-methoxyphenyl)methylene]-7-azaoxindole;

3-[(4-aminophenyl)methylene]-7-azaoxindole;

3-[(4-diethanolaminophenyl)methylene]-7-azaoxindole;

3-[(4-glyceroylamidophenyl)methylene]-7-azaoxindole;

3-[(4-((3-piperidinopropionylamino)phenyl)methylene]-7-azaoxindole;

3-[(4-ureidophenyl)methylene]-7-azaoxindole;

3-[(4-mesylaminophenyl)methylene]-7-azaoxindole;

3-[(4-guanidinophenyl)methylene]-7-azaoxindole;

3-[(4-sulfophenyl)methylene]-7-azaoxindole;

3-[(4-N,N-piperazinylsulfamoylphenyl)methylene]-7-azaoxindole;

3-[4-sulfamoylphenyl)methylene]-7-azaoxindole;

3-[4-aminomethylphenyl)methylene]-7-azaoxindole;

3-[4-amidinophenyl)methylene]-7-azaoxindole;

3-[4-phosphonooxyphenyl)methylene]-7-azaoxindole;

3-[4-carboxyphenyl)methylene]-7-azaoxindole;

3-[4-carbomethoxyphenyl)methylene]-7-azaoxindole;

3-[(4-hydroxymethylphenyl)methylene]-7-azaoxindole;

3-[4-(2,3-dihydroxypropylamino)phenylmethylene]-7-azaoxindole;

3-[(4-glycoloyloxyphenyl)methylene]-7-azaoxindole;

3-[(4-phosphonophenyl)methylene]-7-azaoxindole;

3-[(4-hydroxyethylpiperazin-1-ylmethyl)phenyl methylene]-7-azaoxindole;

3-[4-(N,N-(4'-hydroxyethyl)piperazinylcarbamoyl) phenylmethylene]-7-azaoxindole;

3-[4-sulfophenylmethylene]-7-azaoxindole sodium salt;

3-[4-aminophenylmethylene]-7-azaoxindole hydrochloride;

3-[4-aminophenylmethylene]-7-azaoxindole trifluoroacetate;

3-[(3-hydroxy-5,6,7,8-tetrahydronaphth-2-yl)methylene]-7-azaoxindole;

3-[(1,4-dihydroxy-5,6,7,8-tetrahydronaphth-2-yl)methylene]-7-azaoxindole;

3-[3-(2,3-dihydroxypropoxy)-5,6,7,8-tetrahydronaphth-2-yl)methylene]-7-azaoxindole;

3-[(3-methoxy-5,6,7,8-tetrahydronaphth-2-yl)methylene]-7-azaoxindole;

3-[(4-amino-5,6,7,8-tetrahydronaphth-1-yl)methylene]-7-azaoxindole;

3-[(4-diethanolamino-5,6,7,8-tetrahydronaphth-1-yl)methylene]-7-azaoxindole;

3-[(4-glyceroylamino-5,6,7,8-tetrahydronaphth-1-yl)methylene]-7-azaoxindole;

3-[4-((3-piperidinopropionylamino)-5,6,7,8-tetrahydronaphth-1-yl)methylene]-7-azaoxindole;

3-[(4-ureido-5,6,7,8-tetrahydronaphth-1-yl)methylene]-7-azaoxindole;

3-[(4-mesylamino-5,6,7,8-tetrahydronaphth-1-yl)methylene]-7-azaoxindole;

3-[(4-guanidino-5,6,7,8-tetrahydronaphth-1-yl)methylene]-7-azaoxindole;

3-[(4-sulfo-5,6,7,8-tetrahydronaphth-1-yl)methylene]-7-azaoxindole;

3-[(4-N,N-piperazinylsulfamoyl-5,6,7,8-tetrahydronaphth-1-yl)methylene]-7-azaoxindole;

3-[(4-sulfamoyl-5,6,7,8-tetrahydronaphth-1-yl)methylene]-7-azaoxindole;

3-[(4-aminomethyl-5,6,7,8-tetrahydronaphth-1-yl)methylene]-7-azaoxindole;

3-[(4-amidino-5,6,7,8-tetrahydronaphth-1-yl)methylene]-7-azaoxindole;

3-[(4-phosphono-5,6,7,8-tetrahydronaphth-1-yl)methylene]-7-azaoxindole;

3-[(4-carboxy-5,6,7,8-tetrahydronaphth-1-yl)methylene]-7-azaoxindole;

3-[(4-carbomethoxy-5,6,7,8-tetrahydronaphth-1-yl)methylene]-7-azaoxindole;

3-[(4-quinolyl)methylene]-7-azaoxindole;

3-[(8-hydroxy-5-quinolyl)methylene]-7-azaoxindole;

3-[(8-sulfo-5-quinolyl)methylene]-7-azaoxindole;

3-[(8-sulfamoyl-5-quinolyl)methylene]-7-azaoxindole;

3-[(8-aminomethyl-5-quinolyl)methylene]-7-azaoxindole;

3-[(2-methyl-3-indolyl)methylene]-7-azaoxindole;

3-[(3-indolyl)methylene]-7-azaoxindole;

3-[(5-hydroxy-3-indolyl)methylene]-7-azaoxindole;

3-[(5-methoxy-3-indolyl)methylene]-7-azaoxindole;
3-[(5-amino-3-indolyl)methylene]-7-azaoxindole;
3-[(5-diethanolamino-3-indolyl)methylene]-7-azaoxindole;
3-[(5-glyceroylamido-3-indolyl)methylene]-7-azaoxindole;
3-[(5-(3-piperidinopropionylamino)-3-indolyl)methylene]-7-azaoxindole;
3-[(5-ureido-3-indolyl)methylene]-7-azaoxindole;
3-[(5-mesylamino-3-indolyl)methylene]-7-azaoxindole;
3-[(5-guanidino-3-indolyl)methylene]-7-azaoxindole;
3-[(5-sulfo-3-indolyl)methylene]-7-azaoxindole;
3-[(5-N,N-piperazinylsulfamoyl-3-indolyl)methylene]-7-azaoxindole;
3-[(5-sulfamoyl-3-indolyl)methylene]-7-azaoxindole;
3-[(5-aminomethyl-3-indolyl)methylene]-7-azaoxindole;
3-[(5-amidino-3-indolyl)methylene]-7-azaoxindole;
3-[(5-phosphono-3-indolyl)methylene]-7-azaoxindole;
3-[(5-carboxy-3-indolyl)methylene]-7-azaoxindole;
3-[(5-carbomethoxy-3-indolyl)methylene]-7-azaoxindole;
3-[(7-azaindol-3-yl)methylene]-7-azaoxindole;
3-[(4-hydroxy-7-azaindol-3-yl)methylene]-7-azaoxindole;
3-[(4-amino-7-azaindol-3-yl)methylene]-7-azaoxindole;
3-[(4-((3-piperidinopropionylamino)-7-aziondol-3-yl)methylene]-7-azaoxindole
3-[(4-ureido-7-azaindol-3-yl)methylene]-7-azaoxindole;
3-[(4-sulfo-7-azaindol-3-yl)methylene]-7-azaoxindole;
3-[(4-sulfamoyl-7-azaindol-3-yl)methylene]-7-azaoxindole;
3-[(4-amidino-7-azaindol-3-yl)methylene]-7-azaoxindole;
3-[(4-carboxy-7-azaindol-3-yl)methylene]-7-azaoxindole;
and the pharmaceutically acceptable salt of the above listed compounds.

4. A process for obtaining a compound of formula (I) according to claim 1 or a pharmaceutically acceptable salt thereof, comprising:

a) condensation of an aldehyde of formula (II)

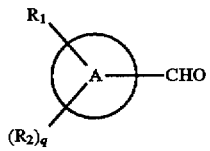

wherein A, $R_1$, $R_2$ and q are as defined in claim 1, with a compound of formula (III)

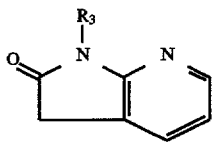

wherein $R_3$ is as defined in claim 1; or b) N-alkylation of a compound of formula (IV)

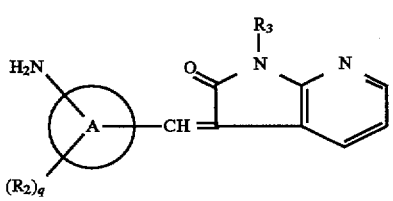

wherein A, $R_2$, $R_3$ and q are as defined in claim 1, thus obtaining a compound of formula (I), wherein $R_1$ is —N(CH$_2$CH$_2$OH)$_2$ or —NHCH$_2$(CHOH)$_n$CH$_2$OH and A, $R_2$, $R_3$ and q are as defined in claim 1; or c) N-acetylation of a compound of formula (IV), wherein A, $R_2$, $R_3$ and q are as defined in claim 1, thus obtaining a compound of formula (I) wherein $R_1$ is —NHCO(CHOH)$_n$CH$_2$OH or

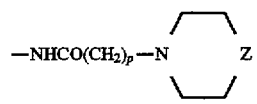

and A, $R_2$, $R_3$, n, p, q and Z are as defined in claim 1; or d) N-sulfonylation of a compound of formula (IV) wherein A, $R_2$, $R_3$ and q are as defined in claim 1, thus obtaining a compound of formula (I) wherein $R_1$ is —NHSO$_2$R$_9$ and A, $R_2$, $R_3$, $R_9$ and q are as defined above; or e) N-amidination of a compound of formula (IV) wherein A, $R_2$, $R_3$ and q are as defined in claim 1, thus obtaining a compound of formula (I) wherein $R_1$ is —NHC(NH$_2$)=NH and A, $R_2$, $R_3$ and q are as defined above; or f) N-carbamoylation of a compound of formula (IV) wherein A, $R_2$, $R_3$ and q are as defined in claim 1, thus obtaining a compound of formula (I) wherein $R_1$ is —NHCONH$_2$ and A, $R_2$, $R_3$ and q are as defined above; or g) O-alkylation of a compound of formula (V)

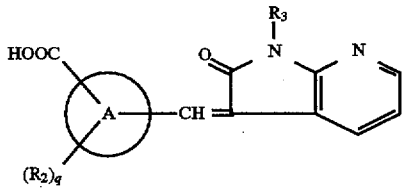

wherein A, $R_2$, $R_3$ and q are as defined in claim 1, thus obtaining a compound of formula (I) wherein $R_1$ is —OCH$_2$(CHOH)$_n$CH$_2$OH or —OR$_{10}$ in which R$_{10}$ is $C_1$–$C_6$ alkyl and A, $R_2$, $R_3$ and q are as defined above; or h) O-acylation of a compound of formula (V) wherein A, $R_2$, $R_3$ and q are as defined in claim 1, thus obtaining a compound of formula (I) wherein $R_1$ is —OOC(CHOH)$_n$CH$_2$OH or —OR$_{10}$ in which R$_{10}$ is $C_2$–$C_6$ alkanoyl and A, $R_2$, $R_3$ and q are as defined above; or i) O-phosphorylation of a compound of formula (V) wherein A, $R_2$, $R_3$ and q are as defined in claim 1, thus obtaining a compound of formula (I) wherein $R_1$ is —OPO(OH)$_2$ and A, $R_2$, $R_3$ and q are as defined above; or k) esterification of a compound of formula (VI)

wherein A, $R_2$, $R_3$ and q are as defined in claim 1, thus obtaining a compound of formula (I) wherein $R_1$ is —COOR$_6$ and A, $R_2$, $R_3$ and q are as defined above; or l) ammonia addition of a compound of formula (VII)

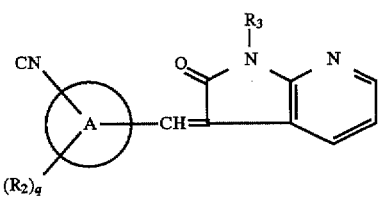
(VII)

wherein A, $R_2$, $R_3$ and q are as defined in claim 1, thus obtaining a compound of formula (I) wherein $R_1$ is —C(NH$_2$)=NH and A, $R_2$, $R_3$ and q are as defined above; or m) amination of a compound of formula (VIII)

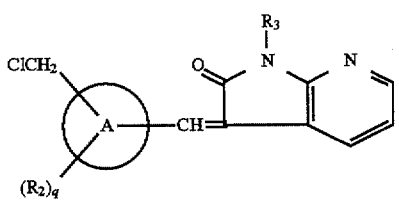
(VIII)

wherein A, $R_2$, $R_3$ and q are as defined in claim 1, thus obtaining a compound of formula (I) wherein $R_1$ is —CH$_2$NH$_2$ or

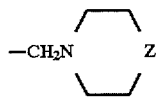

and A, $R_2$, $R_3$ and q are as defined above; and/or conversion of a compound of formula (I) into another compound of formula (I) and/or optional salification of a compound of formula (I) or conversion of a salt into the corresponding free compound of formula (I) and/or, if desired, separation of a mixture of isomers into the single isomers.

5. A pharmaceutical composition containing a suitable carrier and/or diluent and, as an active principle, a compound of formula (I) according to claim 1 or a pharmaceutically acceptable salt thereof.

6. A compound of formula (I) according to claim 1, or a pharmaceutically acceptable salt thereof, for use as a tyrosine kinase inhibitor.

7. A method comprising treating a subject with an effective amount of a compound of formula (I) as defined in claim 1, or a pharmaceutically acceptable salt thereof, as a tyrosine kinase inhibitor.

8. A compound of formula (I) according to claim 1, or a pharmaceutically acceptable salt thereof, for use as antiproliferative agent.

9. A method comprising treating a subject with an effective amount of a compound of formula (I), according to claim 1, or a pharmaceutically acceptable salt thereof, as an antiproliferative agent.

10. A compound of formula (I) according to claim 1, or a pharmaceutically acceptable salt thereof, for use as anti-cancer agent or in the treatment of coronary artery disease or in the control of angiogenesis.

11. A method comprising treating a subject with an effective amount of a compound of formula (I), according to claim 1, or a pharmaceutically acceptable salt thereof, as anti-cancer agent or in the treatment of coronary artery disease or in the control of angiogenesis.

12. Products containing a compound of formula (I), according to claim 1, or a pharmaceutically acceptable salt thereof, and an anti-tumor agent as a combined preparation for simultaneous, separate or sequential use in anti-cancer therapy.

* * * * *